United States Patent
DiGiulio et al.

(10) Patent No.: US 10,843,984 B2
(45) Date of Patent: *Nov. 24, 2020

(54) DEHYDROGENATION PROCESS AT REDUCED HYDROGEN TO HYDROCARBON RATIOS

(71) Applicant: UOP LLC, Des Plaines, IL (US)

(72) Inventors: Christopher DiGiulio, Elmhurst, IL (US); Clayton C. Sadler, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/178,075

(22) Filed: Nov. 1, 2018

(65) Prior Publication Data
US 2019/0127296 A1    May 2, 2019

Related U.S. Application Data

(60) Provisional application No. 62/580,794, filed on Nov. 2, 2017, provisional application No. 62/580,768, filed on Nov. 2, 2017.

(51) Int. Cl.
| | |
|---|---|
| *C07C 5/333* | (2006.01) |
| *B01J 35/02* | (2006.01) |
| *B01J 8/02* | (2006.01) |
| *C07C 5/48* | (2006.01) |
| *C07C 7/04* | (2006.01) |
| *B01J 19/00* | (2006.01) |
| *C07C 11/06* | (2006.01) |

(52) U.S. Cl.
CPC .............. *C07C 5/3337* (2013.01); *B01J 8/02* (2013.01); *B01J 8/0214* (2013.01); *B01J 19/0013* (2013.01); *B01J 35/026* (2013.01); *C07C 5/48* (2013.01); *C07C 7/04* (2013.01); *B01J 2208/00017* (2013.01); *B01J 2208/00539* (2013.01); *B01J 2208/00805* (2013.01); *B01J 2208/00884* (2013.01); *B01J 2208/024* (2013.01); *B01J 2219/00051* (2013.01); *B01J 2219/00195* (2013.01); *C07C 11/06* (2013.01); *C07C 2521/04* (2013.01); *C07C 2523/02* (2013.01); *C07C 2523/08* (2013.01); *C07C 2523/14* (2013.01); *C07C 2523/40* (2013.01); *C07C 2523/42* (2013.01)

(58) Field of Classification Search
CPC ......... C07C 5/3337; C07C 7/04; C07C 11/06; C07C 2523/42; C07C 2521/04; C07C 2523/02; C07C 2523/08; C07C 2523/14; C07C 2523/40; C07C 5/48; B01J 19/0013; B01J 35/026; B01J 8/02; B01J 2219/00051; B01J 2219/00195; B01J 2208/024; B01J 2208/00805; B01J 2208/00884; B01J 8/0214; B01J 2208/00017; B01J 2208/00539
See application file for complete search history.

(56) References Cited

U.S. PATENT DOCUMENTS

| | | | |
|---|---|---|---|
| 3,670,044 | A | 6/1972 | Drehman |
| 4,418,237 | A | 11/1983 | Imai |
| 4,613,715 | A | 9/1986 | Haskell |
| 4,788,371 | A | 11/1988 | Imai et al. |
| 4,914,075 | A | 4/1990 | Bricker et al. |
| 5,324,880 | A | 6/1994 | Dyroff |
| 6,417,135 | B1 * | 7/2002 | Dyroff ............... B01J 23/40 502/20 |
| 6,756,340 | B2 | 6/2004 | Voskoboynikov et al. |
| 8,309,782 | B2 | 11/2012 | Le Peltier et al. |
| 8,895,797 | B2 | 11/2014 | Myers et al. |
| 2005/0033101 | A1 | 2/2005 | Voskoboynikov et al. |
| 2015/0111720 | A1 | 4/2015 | Vaidya et al. |
| 2016/0122263 | A1 * | 5/2016 | Nawaz ............ C07C 5/3332 585/659 |

FOREIGN PATENT DOCUMENTS

| | | |
|---|---|---|
| CN | 1201715 | 12/1998 |
| CN | 105214657 | 1/2016 |
| WO | 2015084041 | 6/2015 |
| WO | 2016005896 | 1/2016 |

* cited by examiner

*Primary Examiner* — Ali Z Fadhel

(57) ABSTRACT

Processes for dehydrogenation of a hydrocarbon feedstock are described. The process can be run at lower $H_2$/HC ratios and lower RITs while maintaining coke production at the same level as operation at higher $H_2$/HC ratios and higher RITs without decreasing the yield per pass. Acceptable levels of coke were achieved when operating the process at low hydrogen to hydrocarbon molar ratio in the range of 0.01 to 0.40 and reactor inlet temperatures in the range of 500°-645° C.

8 Claims, No Drawings

DEHYDROGENATION PROCESS AT REDUCED HYDROGEN TO HYDROCARBON RATIOS

This application claims the benefit of U.S. Provisional Patent Application Ser. No. 62/580,768 filed Nov. 2, 2017, and U.S. Provisional Patent Application Ser. No. 62/580,794 filed Nov. 2, 2017, each of which is hereby incorporated by reference in its entirety.

BACKGROUND

The dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers, and other products which are well known to those skilled in the art. A process for the conversion of paraffins to olefins involves passing a paraffin stream over a highly selective catalyst, where the paraffin is dehydrogenated to the corresponding olefin. The dehydrogenation reaction is achieved under operating conditions selected to minimize the loss of feedstock. The typical process involves the use of a reactor (e.g., radial flow, fixed bed, fluidized bed, and the like) where a paraffin feedstock is contacted with a dehydrogenation catalyst under reaction conditions. One example of this process is the dehydrogenation of isobutane to produce isobutylene which can be polymerized to provide tackifying agents for adhesives, viscosity-index additives for motor oils, and impact-resistant and antioxidant additives for plastics. There is also a growing demand for isobutylene for the production of oxygen-containing gasoline blending components which are being mandated by the government in order to reduce air pollution from automotive emissions.

Those skilled in the art of hydrocarbon conversion processing are well versed in the production of olefins by means of catalytic dehydrogenation of paraffinic hydrocarbons. In addition, many patents have issued which teach and discuss the dehydrogenation of hydrocarbons in general. For example, U.S. Pat. No. 4,430,517 (Imai et al) discusses a dehydrogenation process and catalyst for use therein.

SUMMARY AND DETAILED DESCRIPTION

In paraffin dehydrogenation processes, hydrogen is commonly co-fed to minimize the amount of carbonaceous material deposited on the catalyst and to improve catalyst stability. Practically, the amount of hydrogen co-feed is represented as the hydrogen/hydrocarbon ($H_2$/HC) ratio, which is calculated by dividing the hydrogen molar flowrate by the hydrocarbon molar flowrate. If more than one dehydrogenation reactor is present in series, it is convenient to refer to a $H_2$/HC ratio for the entire process, which is calculated by dividing the hydrogen feed to the first reactor by the hydrocarbon feed to the first reactor. Henceforth, the $H_2$/HC ratio is taken to be synonymous with the $H_2$/HC ratio for the process, which is more precisely defined as the $H_2$/HC ratio in the combined Hydrogen-Hydrocarbon feed stream going to the first, of at least one, dehydrogenation reactor. While hydrogen decreases coking on the catalyst, it also changes the equilibrium conversion of paraffin to the desired olefin at a given temperature and pressure. Thus, there is a trade-off between minimizing catalyst coking and maximizing conversion.

Some dehydrogenation processes utilize a continuous catalyst regeneration (CCR) system to burn off coke. However, there is a practical limit to how quickly catalyst can be circulated through the regenerator system and how much coke can be burned off the catalyst.

Thus, the $H_2$/HC ratio is a significant design parameter used to balance catalyst coking and achieve the most efficient design.

For example, if the $H_2$/HC ratio is lowered and the reactor inlet temperatures (RITs) remain the same, or if the RITs are raised and the $H_2$/HC ratio remains the same, then increased coke on the catalyst would be expected.

However, it was surprisingly discovered that by simultaneously lowering the $H_2$/HC ratio and the RITs, coke production can be maintained at the same level as operation at higher $H_2$/HC ratios and higher RITs without decreasing the yield per pass (YPP), which is a key parameter that affects the overall profitability of the dehydrogenation process. Yield per pass is calculated by dividing the mass flowrate of olefin (e.g. propylene) produced across the reactor section by the mass flowrate of paraffin (e.g., propane) in the feed.

Operation at a lower $H_2$/HC ratio without a reduction in YPP results in lower volumetric flow through the reactor section, thus decreasing the utilities for that section of the process. When combining a reduction in the $H_2$/HC ratio and RITs with a low coke catalyst, the temperature reduction will be less than with a conventional commercial catalyst enabling operation at higher YPP and further improves the profitability of the process.

It has been discovered that a low $H_2$/HC ratio coke index can be determined as a function of reactor inlet temperatures and hydrogen to hydrocarbon molar ratios between 0.01 and 0.40. It was surprisingly found that acceptable levels of coke were achieved when operating at these low hydrogen to hydrocarbon molar ratios.

The low $H_2$/HC coke index is determined by measuring coking for a range of reactor inlet temperatures and hydrogen to hydrocarbon molar ratio combinations. The correlation between the reactor inlet temperature and the hydrogen to hydrocarbon molar ratio can then be determined. This correlation and a selected hydrogen to hydrocarbon molar ratio can be used to determine a desired reactor inlet temperature, and the reactor can be adjusted to the determined reactor inlet temperature. Alternatively, the correlation and a selected reactor inlet temperature can be used to determine a desired hydrogen to hydrocarbon molar ratio, and the hydrogen to hydrocarbon molar ratio can be adjusted to the determined hydrogen to hydrocarbon molar ratio. Alternatively, the coke index can be determined for a selected reactor inlet temperature and a selected hydrogen to hydrocarbon molar ratio.

One aspect of the invention is a process for dehydrogenation of a hydrocarbon feedstock. In one embodiment, the process comprises: passing a feed stream comprising hydrogen and paraffins into a dehydrogenation zone comprising at least one reactor containing a dehydrogenation catalyst maintained at dehydrogenation conditions to produce a dehydrogenation zone product stream comprising hydrogen, paraffins, and olefins; wherein the dehydrogenation conditions in the at least one reactor include a hydrogen to hydrocarbon molar ratio in a range of 0.01 to 0.40 and a reactor inlet temperature in a range of 500°-645° C.

In some embodiments, the hydrogen to hydrocarbon molar ratio is in the range of 0.01-0.35 and the reactor inlet temperature is in the range of 500°-640° C.

In some embodiments, the hydrogen to hydrocarbon molar ratio is in the range of 0.01-0.25 and the reactor inlet temperature is in the range of 500°-630° C.

In some embodiments, the hydrogen to hydrocarbon molar ratio is in the range of 0.01-0.15 and the reactor inlet temperature is in the range of 500°-620° C.

In some embodiments, the process further comprises separating the dehydrogenation zone product stream into a hydrocarbon rich product stream and hydrogen rich product stream.

In some embodiments, the process further comprises passing a portion of the hydrogen rich stream to the dehydrogenation zone.

In some embodiments, the hydrocarbon feed comprises at least one paraffin having 2 to 30 carbon atoms. In some embodiments, the hydrocarbon feed comprises at least one paraffin having 2 to 6 carbon atoms. In some embodiments, the hydrocarbon feed comprises at least one paraffin having 3 to 4 carbon atoms.

In some embodiments, the process further comprises at least one of: sensing at least one parameter of the process and generating a signal or data from the sensing; generating and transmitting a signal; or generating and transmitting data.

Another aspect of the invention is a process for dehydrogenation of a hydrocarbon feedstock. In one embodiment, the process comprises: passing a feed stream comprising hydrogen and paraffins into a dehydrogenation zone comprising at least one reactor containing a dehydrogenation catalyst maintained at dehydrogenation conditions to produce a dehydrogenation zone product stream comprising hydrogen, light ends, paraffins, and olefins; wherein the dehydrogenation conditions in the at least one reactor include a hydrogen to hydrocarbon molar ratio, a reactor inlet temperature, and a coke index, wherein the hydrogen to hydrocarbon molar ratio is in a range of 0.01 to 0.4, and wherein one dehydrogenation condition is adjusted based on the other two dehydrogenation conditions.

In some embodiments, either the reactor inlet temperature is adjusted based on a selected hydrogen to hydrocarbon molar ratio and the coke index or the hydrogen to hydrocarbon molar ratio is adjusted based on a selected reactor inlet temperature and the coke index.

In some embodiments, the coke index is in a range of 0-250.

In some embodiments, the coke index is determined by measuring coking for a range of reactor inlet temperature and hydrogen to hydrocarbon molar ratio combinations and determining a correlation between the reactor inlet temperature and the hydrogen to hydrocarbon molar ratio; and wherein a desired reactor inlet temperature is determined using the correlation and the selected hydrogen to hydrocarbon molar ratio and wherein the reactor inlet temperature is adjusted to the determined reactor inlet temperature; or wherein a desired hydrogen to hydrocarbon molar ratio is determined using the correlation and the selected reactor inlet temperature and wherein the hydrogen to hydrocarbon molar ratio is adjusted to the determined hydrogen to hydrocarbon molar ratio.

In some embodiments, the hydrocarbon feed comprises at least one paraffin having 2 to 30 carbon atoms. In some embodiments, the hydrocarbon feed comprises at least one paraffin having 2 to 6 carbon atoms. In some embodiments, the hydrocarbon feed comprises at least one paraffin having 3 to 4 carbon atoms.

In some embodiments, the process further comprises separating the dehydrogenation zone product stream into a hydrocarbon rich product stream and hydrogen rich product stream.

In some embodiments, the process further comprises passing a portion of the hydrogen rich stream to the dehydrogenation zone.

In some embodiments, the process further comprises at least one of: sensing at least one parameter of the process and generating a signal or data from the sensing; generating and transmitting a signal; or generating and transmitting data.

The dehydrogenation of paraffinic hydrocarbons is well known to those skilled in the art of hydrocarbon processing. Dehydrogenatable hydrocarbons are contacted with a dehydrogenation catalyst in a dehydrogenation zone maintained at dehydrogenation conditions. This contacting may be accomplished in a fixed catalyst bed system, a moving catalyst bed system, a fluidized bed system, etc., or in a batch-type operation. The dehydrogenation zone may comprise one or more separate reaction zones with heating means therebetween to ensure that the desired reaction temperature can be maintained at the entrance to each reaction zone. The hydrocarbon may be contacted with the catalyst bed in either upward, downward, or radial flow fashion. Radial flow of the hydrocarbon through the catalyst bed is preferred for a moving catalyst bed system. Radial flow reactors are constructed such that the reactor has an annular structure and annular distribution and collection devices. The devices for distribution and collection incorporate some type of screened surface. The screened surface is for holding catalyst beds in place and for aiding in the distribution of pressure over the surface of the reactor to facilitate radial flow through the reactor bed. The screen can be a mesh, either wire or other material, or a punched plate. For a moving bed, the screen or mesh provides a barrier to prevent the loss of solid catalyst particles while allowing fluid to flow through the bed. Solid catalyst particles are added at the top, flow through the apparatus, and are removed at the bottom, while passing through a screened-in enclosure that permits the flow of fluid over the catalyst. For example, the screens are described in U.S. Pat. Nos. 9,266,079 and 9,433,909 (Vetter et al.).

Hydrocarbons which may be dehydrogenated include dehydrogenatable hydrocarbons having from 2 to 30 or more carbon atoms including paraffins, alkylaromatics, naphthenes, and olefins. One group of hydrocarbons which can be dehydrogenated with the catalyst is the group of normal paraffins having from 2 to 30 or more carbon atoms. The catalyst is particularly useful for dehydrogenating paraffins having from 2 to 15 or more carbon atoms to the corresponding monoolefins or for dehydrogenating monoolefins having from 3 to 15 or more carbon atoms to the corresponding diolefins. The catalyst is especially useful in the dehydrogenation of $C_2$-$C_6$ paraffins, primarily propane and butanes, to monoolefins.

Light paraffin dehydrogenation utilizes a highly selective platinum-based catalyst system. One example of a suitable catalyst light paraffin dehydrogenation is disclosed in U.S. Pat. No. 6,756,340, which is incorporated herein by reference. Heavier paraffin dehydrogenation uses a selective platinum catalyst.

Dehydrogenation conditions include a temperature of from about 400° to about 900° C., a pressure of from about 0.01 to 10 atmospheres absolute, and a liquid hourly space velocity (LHSV) of from about 0.1 to 100 $hr^{-1}$. Generally, for normal paraffins, the lower the molecular weight, the higher the temperature required for comparable conversion. The pressure in the dehydrogenation zone is maintained as low as practicable, consistent with equipment limitations, to maximize the chemical equilibrium advantages.

The effluent stream from the dehydrogenation zone generally will contain unconverted dehydrogenatable hydrocarbons, hydrogen, and the products of dehydrogenation reactions. This effluent stream is typically cooled, optionally compressed and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions, or by means of a suitable fractionation scheme. Unconverted dehydrogenatable hydrocarbons are recovered and may be recycled to the dehydrogenation zone. Products of the dehydrogenation reactions are recovered as final products or as intermediate products in the preparation of other compounds.

In summary, a dehydrogenation process may include one or more dehydrogenation reactors, fired heaters, heat exchangers, quench towers, compressors, cryogenic separation systems, treatment systems, fuel gas preparation systems, light ends recovery systems, adsorption systems, fractionation columns, catalyst handling/regeneration equipment, as is known in the art and further discussed in "Handbook of Petroleum Refining Process, 4$^{th}$ Edition, Chapter 4.1."

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

EXAMPLE 1

Development of the Coke Index for Propane Dehydrogenation:

A series of catalyst coking experiments were conducted covering a temperature range of 490-650° C. and a $H_2$ to HC ratio range of 0.05 to 0.80. The feed to the catalyst beds comprised mixtures of hydrocarbon and hydrogen.

After each test the catalyst samples were sent for carbon analysis, which was reported as a wt % of the total catalyst sample. Table 1 provides a few illustrative examples of these experiments. As the results in Table 1 show, catalyst coking is a strong function of both temperature and the $H_2$/HC ratio. Thus, a coke index can be created using these two key effects.

Equation 1 summarizes the coke index created using the experiments described above. First, the experiments were sorted into groups of constant $H_2$/HC ratios as a function of temperature. Next, the LN(coke) versus 1/T was plotted for each $H_2$/HC ratio. This provided a unique linear relationship for each $H_2$/HC ratio. Next, the slopes and intercepts of each of these unique linear relationships were plotted as a function of the $H_2$/HC ratio to yield a second set of linear relationships. Finally, these two sets of linear relationships were combined to yield the coke index shown in Equation 1.

$$\text{Coke Index} = e^{\left[\left(-13923 \times \frac{H2}{HC} - 20201\right) \times \left(\frac{1}{T}\right) \times \left(18.63 \times \frac{H2}{HC} + 38.12\right)\right]} \quad \text{Equation 1 (C}_3\text{)}$$

Table 2 illustrates how to make use of this coke index. For the purposes of this example, it is assumed that an operating unit is running at 635° C. and an $H_2$/HC of 0.50, and the amount of coke being formed on the catalyst is within the acceptable range. The plant operator wants to reduce $H_2$/HC to 0.40 and needs to determine how much to lower the temperature such that coke on catalyst is expected to remain essentially the same as in the base case. First, equation 1 is used to calculate the coke index for the base case, which is 105.5 at 635° C. and an $H_2$/HC of 0.50. Next, equation 1 is used again, but this time the coke index and temperature are known and instead the temperature (T) must be solved for to achieve the same coke index as in the base case, with the resulting temperature being approximately 630° C.

TABLE 1

| | Hydrocarbon Feed | $H_2$/HC | Temp., deg C. | Coke, wt % |
| --- | --- | --- | --- | --- |
| Sample 1 | Propane | 0.5 | 590 | 0.40 |
| Sample 2 | Propane | 0.2 | 590 | 1.34 |
| Sample 3 | Propane | 0.2 | 560 | 0.05 |

TABLE 2

| | $H_2$/HC | Temp., deg C. | Coke Index |
| --- | --- | --- | --- |
| Base Case | 0.50 | 635 | 105.5 |
| Target Operation | 0.40 | 630 | 106.2 |

EXAMPLE 2

Use of the Coke Index for Propane Dehydrogenation Process:

A case study was rigorously simulated using commercially available process simulator (such as Aspen or Unisim)

to demonstrate how the coke index can be used to select reactor inlet temperatures for a new $H_2/HC$ ratio target. The results of the simulation are shown in Table 3.

TABLE 3

| | $H_2/HC$ Molar ratio | Rx Inlet Temps °C. | Selectivity wt % | Yield Per Pass wt % |
|---|---|---|---|---|
| Base Case | 0.5 | Base | Base | Base |
| Coke Index Results | 0.4 | Base − 5 | Base + 1% | Base ± 1% |

The results shown in Table 3 have been normalized such that all comparisons are made on a relative basis to the base case. In this example the objective was to reduce $H_2/HC$ from 0.5 to 0.4. Reactor inlet temperatures were selected according to the methodology outlined in Example 1. The coke index indicated that reactor inlet temperatures needed to be reduced by ~5° C. After obtaining the reactor inlet temperature settings for the lower $H_2/HC$ case, a second simulation at 0.4 $H_2/HC$ with the updated reactor inlet temperatures was performed. As the results of the table show, the yield per pass remained approximately constant and selectivity to propylene improved. In propane dehydrogenation it is common to have 3-4 reactors in series. Thus, the reactor inlet temperatures for all the reactors were reduced by 5° C. to produce the results shown in the table (i.e., if all reactors were operating at 600 then they all would need to be reduced to 595° C.). In summary, coke on catalyst would not be expected to increase, yield per pass remained essentially the same and selectivity to propylene increased, which improves the profitability of the dehydrogenation process.

EXAMPLE 3

Use of the Coke Index for Isobutane and n-Butane Process:

Use of a coke index is not exclusive to propane dehydrogenation. The same approach can be extended to isobutane and n-butane dehydrogenation. The process simulation disclosed in Example 2 contains a rigorous catalyst coking model used to predict the amount of coke on catalyst expected at the exit of the last reactor. It requires similar inputs as the coke index (i.e., $H_2/HC$ ratio, reactor inlet temperature, hydrocarbon feed composition). The process simulation also contains a dehydrogenation model that runs concurrently with the catalyst coking model. The dehydrogenation model is used to predict the temperature within the catalyst bed and the amount of hydrogen and olefin produced across the catalyst bed. Both models were developed using appropriate kinetic expressions known to those skilled in art of chemical reactor engineering. When combined, these two models can be used to estimate the amount of coke produced, selectivity and yield per pass for a set of proposed operating conditions. The results of the process simulation for three different feeds, with the same RITs and number of reactors are shown in Table 4.

TABLE 4

| FEED | $H_2/HC$ Molar ratio | Rx Inlet Temps °C. | Coke on Catalyst wt % | Yield Per Pass wt % |
|---|---|---|---|---|
| C3 | 0.4 | Base | Base | Base |
| iC4 | 0.4 | Base | Base × 0.6 | Base + 16% |
| nC4 | 0.4 | Base | Base × 2.0 | Base + 16% |

The results shown in Table 4 have been normalized relative to a propane dehydrogenation process. An isobutane dehydrogenation process operating under the same conditions as a propane dehydrogenation process would be expected to make less coke at significantly higher yield per pass. The higher yield per pass is expected as it becomes progressively easier to dehydrogenate hydrocarbons with a higher number of carbon atoms. Comparatively, an n-butane dehydrogenation process operating under the same conditions as a propane dehydrogenation process would be expected to make more coke at the same yield per pass as the isobutane dehydrogenation process.

Coke index equations can additionally be developed using the rigorous coking model embedded with process simulation disclosed in Example 2. First, the process model is used to simulate the experiments performed in Example 1. Next, the same procedures for sorting and plotting the data are followed in order to yield three new coking indexes shown in Equations 2-4.

$$\text{Coke Index} = e^{[(-1140 \times \frac{H2}{HC} - 19841) \times (\frac{1}{T}) + (-1.11 \times \frac{H2}{HC} + 35.30)]} \quad \text{Equation 2 (}C_3\text{)}$$

$$\text{Coke Index} = e^{[(215 \times \frac{H2}{HC} - 19660) \times (\frac{1}{T}) + (-2.88 \times \frac{H2}{HC} + 34.57)]} \quad \text{Equation 3 (}iC_4\text{)}$$

$$\text{Coke Index} = e^{[(-1125 \times \frac{H2}{HC} - 24496) \times (\frac{1}{T}) + (0.06 \times \frac{H2}{HC} + 43.82)]} \quad \text{Equation 4 (}nC_4\text{)}$$

Table 5 summarizes the results of using the coke index estimated from the process simulator (Equation 2) instead of the coke index obtained from experimental data (Equation 1). The coke index for the same scenario (635° C. and an $H_2/HC$ of 0.50) is 13.5. In order to obtain the same coke index at a $H_2/HC$ of 0.40, the temperature must be reduced to approximately 629° C. Thus, the resulting temperature adjustments were the same, within the margin of equipment error, even though the coke index equations were different.

TABLE 5

| | $H_2/HC$ | Temp., deg C. | Coke Index |
|---|---|---|---|
| Base Case | 0.50 | 635 | 13.5 |
| Target Operation | 0.40 | 629 | 13.3 |

In summary, the advantage of the process simulation model is that it can provide predictions over a broad range of proposed operating conditions and feed compositions. The advantage of the coke index is that it only requires the reactor inlet temperature and $H_2/HC$ ratio. However, each hydrocarbon feed composition may require a customized coke index. Finally, the process simulation model and/or coke index can be used to obtain suitable pairs of $H_2/HC$ ratios and reactor inlet temperatures that result in a profitable dehydrogenation process operating without excessive catalyst coking, as summarized in Table 6.

TABLE 6

| $H_2/HC$ Molar Ratio | Rx Inlet Temps, deg C. | |
|---|---|---|
| | $C_3$ & $iC_4$ | $nC_4$ Range |
| 0.01-0.40 | | 525-645 |
| 0.35-0.40 | 585-645 | 555-625 |
| 0.25-0.35 | 575-640 | 545-620 |
| 0.15-0.25 | 565-630 | 535-610 |
| 0.01-0.15 | 555-620 | 525-600 |

Specific Embodiments

While the following is described in conjunction with specific embodiments, it will be understood that this description is intended to illustrate and not limit the scope of the preceding description and the appended claims.

A first embodiment of the invention is a process for dehydrogenation of a hydrocarbon feedstock, the process comprising passing a feed stream comprising hydrogen and paraffins into a dehydrogenation zone comprising at least one reactor containing a dehydrogenation catalyst maintained at dehydrogenation conditions to produce a dehydrogenation zone product stream comprising hydrogen, paraffins, and olefins; wherein the dehydrogenation conditions in the at least one reactor include a hydrogen to hydrocarbon molar ratio in a range of 0.01 to 0.40 and a reactor inlet temperature in a range of 500°-645° C. An embodiment of the invention is one, any or all of prior embodiments in this paragraph up through the first embodiment in this paragraph wherein the hydrogen to hydrocarbon molar ratio is in the range of 0.01-0.35 and the reactor inlet temperature is in the range of 500°-640° C. An embodiment of the invention is one, any or all of prior embodiments in this paragraph up through the first embodiment in this paragraph wherein the hydrogen to hydrocarbon molar ratio is in the range of 0.01-0.25 and the reactor inlet temperature is in the range of 500°-630° C. An embodiment of the invention is one, any or all of prior embodiments in this paragraph up through the first embodiment in this paragraph wherein the hydrogen to hydrocarbon molar ratio is in the range of 0.01-0.15 and the reactor inlet temperature is in the range of 500°-620° C. An embodiment of the invention is one, any or all of prior embodiments in this paragraph up through the first embodiment in this paragraph further comprising separating the dehydrogenation zone product stream into a hydrocarbon rich product stream and hydrogen rich product stream. An embodiment of the invention is one, any or all of prior embodiments in this paragraph up through the first embodiment in this paragraph further comprising passing a portion of the hydrogen rich stream to the dehydrogenation zone. An embodiment of the invention is one, any or all of prior embodiments in this paragraph up through the first embodiment in this paragraph wherein the hydrocarbon feed comprises at least one paraffin having 2 to 30 carbon atoms. An embodiment of the invention is one, any or all of prior embodiments in this paragraph up through the first embodiment in this paragraph wherein the hydrocarbon feed comprises at least one paraffin having 2 to 6 carbon atoms. An embodiment of the invention is one, any or all of prior embodiments in this paragraph up through the first embodiment in this paragraph wherein the hydrocarbon feed comprises at least one paraffin having 3 to 4 carbon atoms. An embodiment of the invention is one, any or all of prior embodiments in this paragraph up through the first embodiment in this paragraph, further comprising at least one of sensing at least one parameter of the process and generating a signal or data from the sensing; generating and transmitting a signal; or generating and transmitting data.

A second embodiment of the invention is a process for dehydrogenation of a hydrocarbon feedstock, the process comprising passing a feed stream comprising hydrogen and paraffins into a dehydrogenation zone comprising at least one reactor containing a dehydrogenation catalyst maintained at dehydrogenation conditions to produce a dehydrogenation zone product stream comprising hydrogen, light ends, paraffins, and olefins; wherein the dehydrogenation conditions in the at least one reactor include a hydrogen to hydrocarbon molar ratio, a reactor inlet temperature, and a coke index, wherein the hydrogen to hydrocarbon molar ratio is in a range of 0.01 to 0.4, and wherein one dehydrogenation condition is adjusted based on the other two dehydrogenation conditions. An embodiment of the invention is one, any or all of prior embodiments in this paragraph up through the second embodiment in this paragraph wherein either the reactor inlet temperature is adjusted based on a selected hydrogen to hydrocarbon molar ratio and the coke index or the hydrogen to hydrocarbon molar ratio is adjusted based on a selected reactor inlet temperature and the coke index. An embodiment of the invention is one, any or all of prior embodiments in this paragraph up through the second embodiment in this paragraph wherein the coke index is in a range of 0-250. An embodiment of the invention is one, any or all of prior embodiments in this paragraph up through the second embodiment in this paragraph wherein the coke index is determined by measuring coking for a range of reactor inlet temperature and hydrogen to hydrocarbon molar ratio combinations and determining a correlation between the reactor inlet temperature and the hydrogen to hydrocarbon molar ratio; and wherein a desired reactor inlet temperature is determined using the correlation and the selected hydrogen to hydrocarbon molar ratio and wherein the reactor inlet temperature is adjusted to the determined reactor inlet temperature; or wherein a desired hydrogen to hydrocarbon molar ratio is determined using the correlation and the selected reactor inlet temperature and wherein the hydrogen to hydrocarbon molar ratio is adjusted to the determined hydrogen to hydrocarbon molar ratio. An embodiment of the invention is one, any or all of prior embodiments in this paragraph up through the second embodiment in this paragraph wherein the hydrocarbon feed comprises at least one paraffin having 2 to 30 carbon atoms. An embodiment of the invention is one, any or all of prior embodiments in this paragraph up through the second embodiment in this paragraph wherein the hydrocarbon feed comprises at least one paraffin having 2 to 6 carbon atoms. An embodiment of the invention is one, any or all of prior embodiments in this paragraph up through the second embodiment in this paragraph wherein the hydrocarbon feed comprises at least one paraffin having 3 to 4 carbon atoms. An embodiment of the invention is one, any or all of prior embodiments in this paragraph up through the second embodiment in this paragraph further comprising separating the dehydrogenation zone product stream into a hydrocarbon rich product stream and hydrogen rich product stream. An embodiment of the invention is one, any or all of prior embodiments in this paragraph up through the second embodiment in this paragraph further comprising passing a portion of the hydrogen rich stream to the dehydrogenation zone. An embodiment of the invention is one, any or all of prior embodiments in this paragraph up through the second embodiment in this paragraph, further comprising at least one of sensing at least one parameter of the process and generating a signal or data from the sensing; generating and transmitting a signal; or generating and transmitting data.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for dehydrogenation of a hydrocarbon feedstock, the process comprising:

passing a feed stream comprising hydrogen and paraffins into a dehydrogenation zone comprising at least one reactor containing a dehydrogenation catalyst maintained at dehydrogenation conditions to produce a dehydrogenation zone product stream comprising hydrogen, light ends, paraffins, and olefins;

wherein the dehydrogenation conditions in the at least one reactor include a hydrogen to hydrocarbon molar ratio, a reactor inlet temperature, and a coke index, wherein the hydrogen to hydrocarbon molar ratio is in a range of 0.01 to 0.4, and wherein one dehydrogenation condition is adjusted based on the other two dehydrogenation conditions;

wherein the coke index is determined by measuring coking for a range of reactor inlet temperature and hydrogen to hydrocarbon molar ratio combinations and determining a correlation between the reactor inlet temperature and the hydrogen to hydrocarbon molar ratio; and wherein a desired reactor inlet temperature is determined using the correlation and the selected hydrogen to hydrocarbon molar ratio and wherein the reactor inlet temperature is adjusted to the determined reactor inlet temperature; or wherein a desired hydrogen to hydrocarbon molar ratio is determined using the correlation and the selected reactor inlet temperature and wherein the hydrogen to hydrocarbon molar ratio is adjusted to the determined hydrogen to hydrocarbon molar ratio.

2. The process of claim 1 wherein either the reactor inlet temperature is adjusted based on a selected hydrogen to hydrocarbon molar ratio and the coke index or the hydrogen to hydrocarbon molar ratio is adjusted based on a selected reactor inlet temperature and the coke index.

3. The process of claim 1 wherein the coke index is in a range of 0-250.

4. The process of claim 1 wherein the hydrocarbon feed comprises at least one paraffin having 2 to 30 carbon atoms.

5. The process of claim 1 wherein the hydrocarbon feed comprises at least one paraffin having 2 to 6 carbon atoms.

6. The process of claim 1 wherein the hydrocarbon feed comprises at least one paraffin having 3 to 4 carbon atoms.

7. The process of claim 1 further comprising separating the dehydrogenation zone product stream into a hydrocarbon rich product stream and hydrogen rich product stream.

8. The process of claim 7 further comprising passing a portion of the hydrogen rich stream to the dehydrogenation zone.

* * * * *